(12) United States Patent
Rajan et al.

(10) Patent No.: US 9,031,641 B2
(45) Date of Patent: May 12, 2015

(54) QUANTIFYING LASER-DOPPLER PERFUSION SIGNAL FOR ARRHYTHMIA DETECTION AND DISEASE MONITORING

(75) Inventors: Vinayakrishnan Rajan, Maastricht (NL); Raphael Alexander Schneider, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 570 days.

(21) Appl. No.: 13/193,059

(22) Filed: Jul. 28, 2011

(65) Prior Publication Data

US 2013/0030307 A1    Jan. 31, 2013

(51) Int. Cl.
| | |
|---|---|
| A61B 5/02 | (2006.01) |
| A61B 5/026 | (2006.01) |
| A61B 5/00 | (2006.01) |
| A61N 1/39 | (2006.01) |
| A61N 1/365 | (2006.01) |
| A61B 5/0205 | (2006.01) |
| A61B 5/022 | (2006.01) |
| A61B 5/046 | (2006.01) |
| A61B 5/0464 | (2006.01) |
| A61N 1/372 | (2006.01) |

(52) U.S. Cl.
CPC .............. *A61B 5/0024* (2013.01); *A61B 5/0261* (2013.01); *A61N 1/3925* (2013.01); *A61B 5/4836* (2013.01); *A61N 1/3962* (2013.01); *A61N 1/36571* (2013.01); *A61B 5/686* (2013.01); *A61B 5/02055* (2013.01); *A61B 5/02233* (2013.01); *A61B 5/046* (2013.01); *A61B 5/0464* (2013.01); *A61B 5/6824* (2013.01); *A61N 1/37211* (2013.01); *A61B 5/0075* (2013.01); *A61B 2560/0209* (2013.01); *A61B 2560/0223* (2013.01); *A61B 2560/0252* (2013.01)

(58) Field of Classification Search
None
See application file for complete search history.

(56) References Cited

U.S. PATENT DOCUMENTS

| | | | |
|---|---|---|---|
| 4,596,254 A * | 6/1986 | Adrian et al. | 600/479 |
| 5,601,611 A | 2/1997 | Fayram | |
| 5,865,749 A | 2/1999 | Doten | |
| 6,259,947 B1 | 7/2001 | Olson | |
| 7,013,178 B2 | 3/2006 | Reinke | |
| 7,092,759 B2 | 8/2006 | Nehls | |
| 7,097,618 B1 | 8/2006 | Benditt | |
| 7,139,613 B2 | 11/2006 | Reinke | |
| 7,529,583 B1 | 5/2009 | Brockway | |
| 7,580,752 B2 | 8/2009 | Gerber | |
| 7,684,864 B2 | 3/2010 | Olson | |
| 7,708,695 B2 | 5/2010 | Akkermans | |
| 7,769,451 B2 | 8/2010 | Yang | |
| 7,894,894 B2 | 2/2011 | Stadler | |
| 2002/0115935 A1* | 8/2002 | Shani et al. | 600/476 |

(Continued)

OTHER PUBLICATIONS

R. F. Bonner and R. Nossal "Model for laser Doppler measurements of blood flow in tissue," Appl. Opt., 1981 2097-2107, vol. 20.

*Primary Examiner* — Long V Le
*Assistant Examiner* — Bradley Impink
(74) *Attorney, Agent, or Firm* — Michael C. Soldner

(57) ABSTRACT

A medical device system and associated method to control a laser Doppler unit to emit light from a coherent laser light source and collect a photodetector signal produced by the laser Doppler unit by a signal processor comprising a bandpass filter. The bandpass filter is applied to the photodetector signal to determine a tissue perfusion measurement from the filtered signal. A monitoring unit is enabled to receive the tissue perfusion measurement to detect a physiological condition of the patient in response to the tissue perfusion measurement.

19 Claims, 10 Drawing Sheets

(56) References Cited

U.S. PATENT DOCUMENTS

| | | | |
|---|---|---|---|
| 2003/0212316 A1* | 11/2003 | Leiden et al. | 600/323 |
| 2007/0129769 A1 | 6/2007 | Bourget | |
| 2008/0081963 A1 | 4/2008 | Naghavi | |
| 2008/0208066 A1* | 8/2008 | Cinbis et al. | 600/504 |
| 2009/0163968 A1 | 6/2009 | Donofrio | |
| 2009/0209871 A1 | 8/2009 | Ueki | |

* cited by examiner

QUANTIFYING LASER-DOPPLER PERFUSION SIGNAL FOR ARRHYTHMIA DETECTION AND DISEASE MONITORING

FIELD OF THE DISCLOSURE

This disclosure relates generally to medical devices and, in particular, to an apparatus and method for monitoring tissue perfusion using laser Doppler flowmetry (LDF).

BACKGROUND

Implantable physiological sensors are used for monitoring patient conditions and for managing or controlling therapies delivered to a patient. For example, there are numerous reasons that a clinician is interested in monitoring the hemodynamic status of a patient. Various implantable sensors such as blood pressure sensors, oxygen sensors, impedance sensors, acoustical sensors or the like have been proposed or used to monitor physiological signals in the body to obtain surrogate measures for cardiac output or other clinical hemodynamic parameters. Reliable, ambulatory monitoring of a hemodynamic parameter can be useful in controlling numerous types of device delivered therapies, such as cardiac resynchronization therapy (CRT) used to treat heart failure or cardioversion and defibrillation shocks used to treat hemodynamically unstable arrhythmias. A need remains for miniaturized physiological sensors that have low power requirements and provide reliable sensing of signals that can be used to monitor the hemodynamic status of a patient

DETAILED DESCRIPTION

In the following description, references are made to illustrative embodiments. It is understood that other embodiments may be utilized without departing from the scope of the disclosure. As used herein, the terms "module" and "unit" refers to an application specific integrated circuit (ASIC), an electronic circuit, a processor (shared, dedicated, or group) and memory that execute one or more software or firmware programs, a combinational logic circuit, and or other suitable components or hardware that provide the described functionality.

Figure 1:
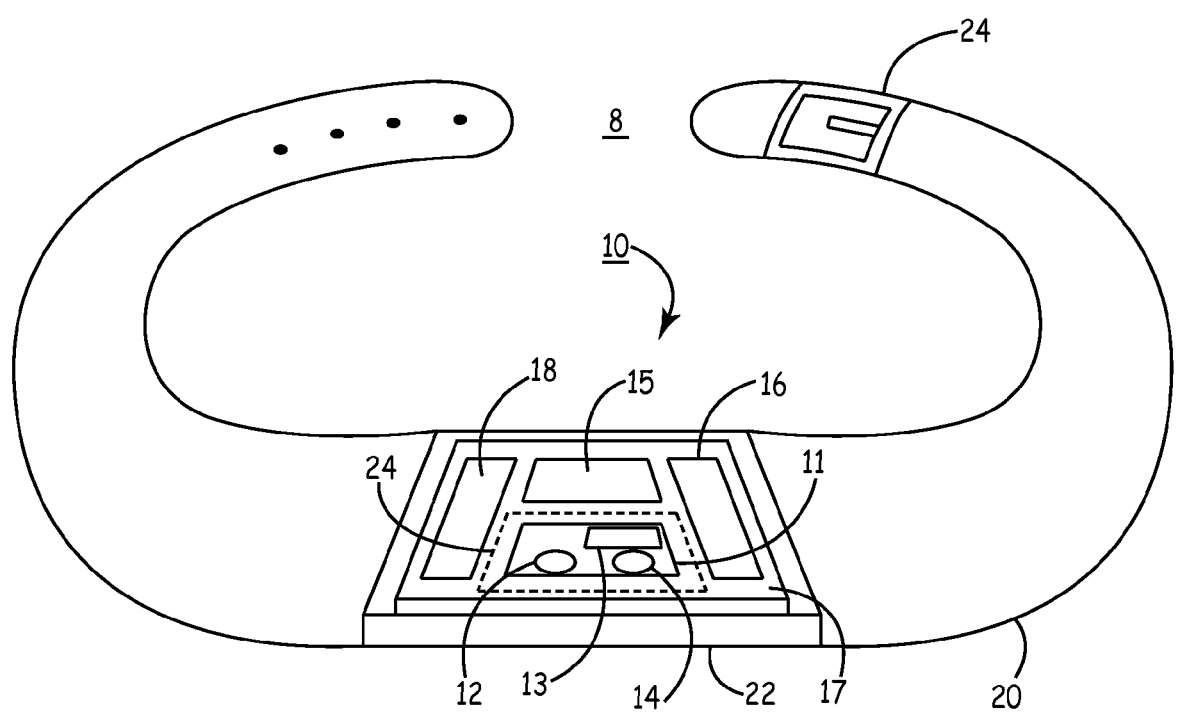
FIG. 1 is a block diagram of a tissue perfusion monitor according to one embodiment.

FIG. 1 is a block diagram of a tissue perfusion monitor 8 according to one embodiment. Tissue perfusion monitor 8 is configured as a wearable, external tissue perfusion monitor including a laser Doppler (LD) tissue perfusion sensor module 10 coupled to a wearable cuff 20. Wearable cuff 20 includes a fastener 24 for stably fastening cuff 20 around a part of the patient's body, such as a limb. For example, cuff 20 may be sized for wearing around a patient's wrist. Wearable cuff 20 is shown as a band with a buckle type fastener but may alternatively be provided in the form of a band with a Velcro, laced, snap, or other type of fastener to stably position cuff 20 around a portion of the patient's body, which may be around a leg, finger, abdomen, thorax, cranium, neck or other body part. Alternatively, cuff 20 may be formed from an elastic material for securely fitting cuff 20 around a body part without the use of a fastener 24.

LD perfusion sensor module 10 includes a housing 22 enclosing circuitry for performing laser Doppler flowmetry (LDF). Housing 22 is coupled to cuff 20. LD module 10 includes a LDF unit 11, a processor 15, and communication circuitry 16. A power source 18, which may be provided as a rechargeable or replaceable battery, provides power to the LDF unit 11, processor and control 15, communication circuitry 16 and any other components requiring power that may be included in module 10. In one embodiment, power source 18 is embodied as a rechargeable Li-ion battery pack providing power for the laser light source 12 and photodetector 14 included in LDF unit 11. It is recognized that in some embodiments, more than one battery may be provided for separately powering the LDF unit 11 and other module components (e.g., processor and control 15 and communication circuitry 16). When multiple batteries are included, any combination of rechargeable and replaceable batteries may be used.

Laser light source 12 is provided as a miniaturized coherent laser light source, such as a laser diode or vertical cavity surface emitting laser (VCSEL). To perform LDF, only a single light source is required. The laser light source is selected to provide a coherent beam of light centered on a wavelength in the visible to near infrared range, for example between approximately 600 and 1300 nm, though other wavelengths may be used successfully in obtaining a tissue perfusion measurement signal. The light source is provided with a narrow bandwidth of the emitted light wavelength, for example a spectral bandwidth of approximately 5 nm or less. In one embodiment, laser light source 12 is embodied is a VCSEL measuring approximately $300 \times 300 \times 150$ μm$^3$, and emitting approximately 1 mW of light at a nominal wavelength of 785 nm and spectral width of approximately 0.8 nm. Processor 15 controls power supply 18 to deliver power to light source 12 when a tissue perfusion measurement is desired. The laser light source 12 is generally selected to have a low power consumption to reduce the battery size and/or increase longevity of the tissue perfusion monitor 10.

Photodetector 14 may be embodied as a photodiode, such as a PIN photodiode. In one embodiment, photodetector 14 is embodied as a PIN photodiode measuring approximately $100 \times 100$ μm$^2$ and having approximately 0.15 A/W sensitivity at 780 nm. Other components suitable for use as a light detector include a photoresistor, phototransistor, photovoltaic cell, photomultiplier tube, bolometer, charge-coupled device (CCD) or an LED reverse-biased to function as a photodiode. Laser light source 12 and photodetector 14 may be integrated in a LDF hybrid circuit unit 11 that additionally includes photodetector conditioning circuitry 13, typically including an amplifier and filter. LDF unit 11 measures approximately 2×2 cm$^2$ in one embodiment and is mounted along a substrate 17, which may be a hybrid circuit board substrate carrying other sensor electronic components. Power source 18, processor and control 15, and communication circuitry 16 are additionally mounted along substrate 17 with appropriate electrical connection provided between the components of module 10 to achieve the functionality described herein.

Light emitted by laser light source 12 is scattered back to photodetector 14 causing an induced photodetector current signal. At least some of the back-scattered light is reflected off moving red blood cells producing a Doppler shifted component of the received light signal. An amplified and filtered photodetector signal is provided by conditioning circuitry 13 to processor 15. The photodetector signal is typically a current signal, but may be measured as a voltage signal in some embodiments.

Processor 15 controls emission of light by laser light source 12 and receives a signal generated by photodetector 14 in response to the back-scattered light. Processor 15 computes or derives a tissue perfusion measurement in response to the Doppler-shifted component of the photodetector current signal, which is correlated to the flow of blood in an adjacent tissue volume. According to techniques disclosed herein, the photodetector signal is filtered using one or more narrowband bandpass filters included in conditioning circuitry 13. The processor determines the magnitude of the filtered signal in the narrow frequency band(s), which is sampled to obtain perfusion measurements. By selecting a narrow bandwidth filter and sampling the filter output at a relatively low frequency, for example on the order of approximately 1 Hz, the power burden and processing power needed to perform normal spectral analysis a LDF signal are greatly reduced while still yielding a reliable relative measurement of tissue perfusion.

In some embodiments, the sensor module 10 may be calibrated to yield standardized measurements. The perfusion signal can be measured when the sensor module 10 is placed along a tissue phantom having a known concentration of a suspension. The tissue perfusion signal measured at one or more known concentrations may then be reported in standardized tissue perfusion units according to a known linear or non-linear response of the tissue perfusion signal to changes in perfusion. The tissue phantom may be designed to mimic pulsatile motion of blood with adjustable flow speeds. Sensor modules may be standardized in this way at the time of manufacture or prior to being positioned in or on a patient so that perfusion signal magnitudes are comparable between sensors and devices.

Communication circuitry 16 includes wireless transmission and receiving circuitry and an associated antenna for sending data to and receiving data from another device. Examples of medical device wireless communication systems that may be employed by the system of the present disclosure include, but are not limited to, the systems disclosed in commonly-assigned U.S. Pat. No. 7,013,178 (Reinke et al.) and U.S. Pat. No. 7,139,613 (Reinke et al.), the disclosures of which are incorporated herein by reference in their entirety. Communication circuitry 16 is controlled by processor 15 to transmit perfusion signal data. Communication circuitry 16 may receive commands or requests for performing perfusion measurements from an external device or an implanted device, such as an ICD or pacemaker adapted for bidirectional communication with sensor module 10.

Figure 2:
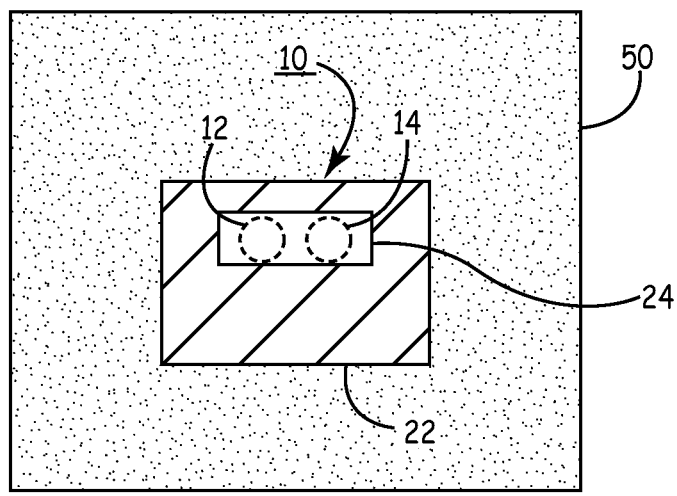
FIG. 2 is a bottom view of an alternative embodiment of a tissue perfusion monitor.

FIG. 2 is a bottom view of an alternative embodiment of a tissue perfusion monitor. Sensor module 10 is coupled to an adhesive patch 50 which may be worn by the patient on his or her skin. As described previously, sensor module 10 includes a housing 22 enclosing sensor circuitry, including laser light source 12 and photodetector 14 shown visible through a lens 24 positioned in an opening formed in housing 22 for passing emitted and back-scattered light. Lens 24 may be formed as a flat panel, cylinder or half-cylinder of glass, sapphire, ruby, quartz or any other suitable light transparent material. In some embodiments, a light barrier may be required between the light source 12 and the photodetector 14 to minimize light from the light source reaching the photodetector 14 directly.

Figure 3:
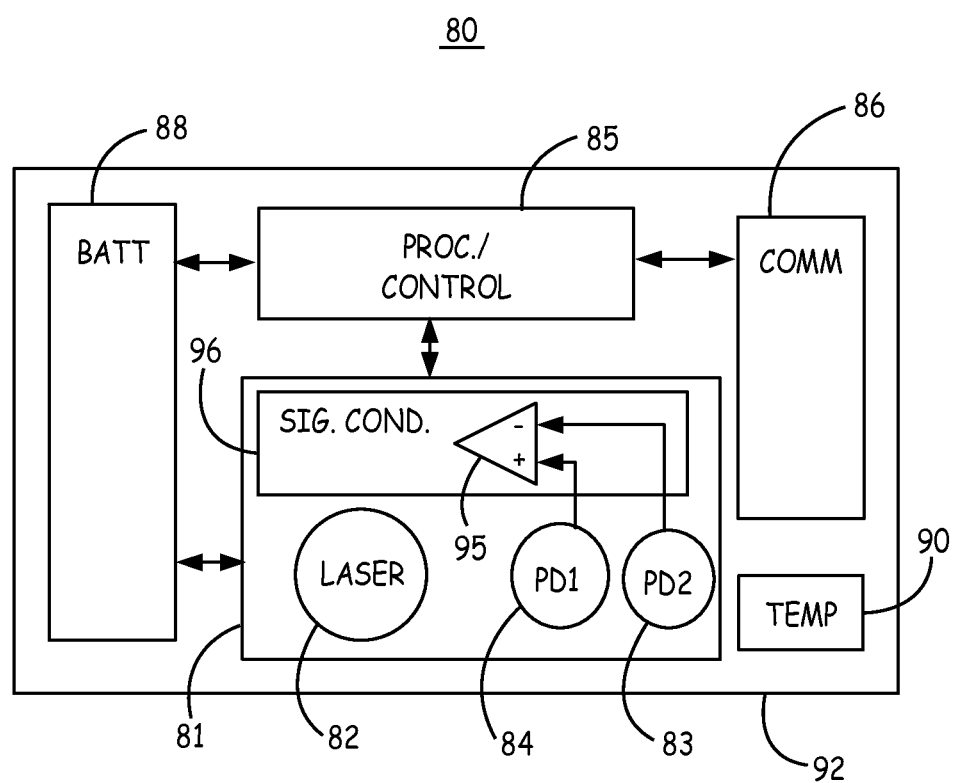
FIG. 3 is a functional block diagram of a tissue perfusion sensor module, according to one embodiment.

FIG. 3 is a functional block diagram of a LD sensor module 80, according to an alternative embodiment. Module 80 includes a LDF unit 81 having a laser light source 82, a first photodetector 84, a second photodetector 83, and signal conditioning circuitry 96. The second photodetector 83 is positioned adjacent the first photodetector 84 to collect substantially the same light signal. Signal conditioning circuitry 96 is shown to include a differential amplifier 95. The differential amplifier 95 rejects common mode noise while still retaining the Doppler shifted light signal associated with moving blood cells in the adjacent tissue. Common mode noise may include laser light source noise 82 common to both photodetector channels (i.e. both photodetector signals).

Sensor module 80 further includes a battery 88 for powering the various sensor module components, such as laser light source 82, processor and control 85, communication circuitry 86 and a temperature sensor 90. Connections between some components shown in module 80 are shown and other connections are not shown for the sake of clarity. It is understood that components shown in module 80 are in electrical connection with each other, for example along a hybrid circuit board 92, as needed to perform the functionality described herein.

Processor and control 85 controls the emission of light by laser source 82 and receives a signal from signal conditioning circuitry 96 for processing and computation of a tissue perfusion measurement. A tissue perfusion measurement signal or parameter values derived therefrom are provided to communication circuitry 86 for transmission to another device.

Temperature sensor 90 is included in module 80 for measuring temperature at the tissue perfusion measurement site. Since blood flow will vary with temperature, a temperature signal is provided to processor and control 85 for use in adjusting or correcting a tissue perfusion measurement signal for the effects of temperature changes. Temperature data may also be provided to communication circuitry 86 for transmission to another device with accompanying tissue perfusion data.

Figure 4:
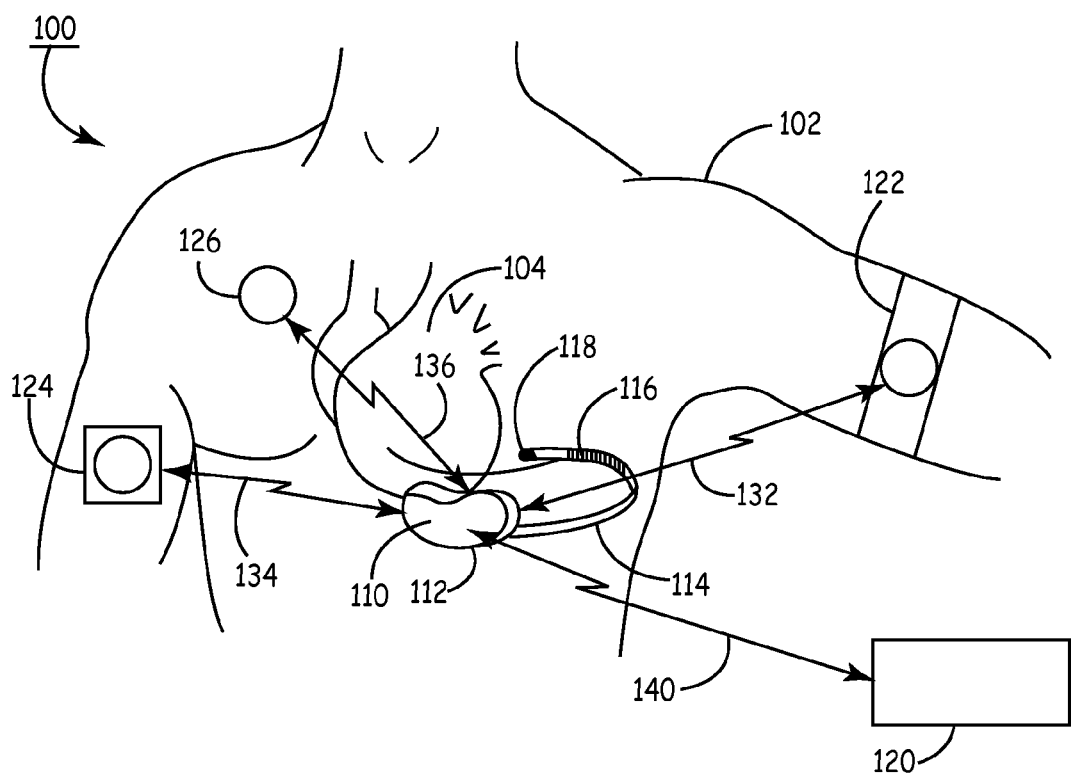
FIG. 4 is a schematic diagram of an implantable medical device system including a tissue perfusion sensor module.

FIG. 4 is a schematic diagram of an implantable medical device (IMD) system 100 including a tissue perfusion sensor module. As illustrated in FIG. 4, an IMD embodied as an ICD 110 is provided as a subcutaneous device in which both the ICD 110 and an associated lead 114 carrying a defibrillation coil electrode 116 are implanted outside the ribcage of the patient 102, subcutaneously or submuscularly. It is understood that while the subcutaneous ICD 110 may be positioned between the skin and muscle layer of the patient, the term "subcutaneous ICD" or generally a "subcutaneously" implantable device as referred to herein is intended to include a device and any associated leads that can be positioned in any extravascular location of the patient, such as below the muscle layer or within the thoracic cavity, for example.

Subcutaneous ICD 110 includes a housing 112 to enclose electronic circuitry of the device 110. Subcutaneous ICD 110 may correspond to a subcutaneous ICD as generally disclosed in U.S. Pat. No. 7,684,864 (Olson et al.) or U.S. Pat. No.

7,894,894 (Stadler, et al.), both of which patents are hereby incorporated herein by reference in their entirety.

A sensing and cardioversion/defibrillation therapy delivery lead 114 in electrical communication with subcutaneous ICD 110 is tunneled subcutaneously into a location adjacent to a portion of a latissimus dorsi muscle of patient 102. Specifically, lead 114 is tunneled subcutaneously from the median implant pocket of the subcutaneous device 110 laterally and posteriorly to the patient's back to a location opposite the heart 104 such that the heart 104 is disposed between the subcutaneous ICD 110 and the distal electrode coil 116 and distal sensing electrode 118 of lead 114 to enable cardioversion/defibrillation shock delivery and cardiac signal sensing. ICD 110 may incorporate sensing electrodes along the housing 112.

A programmer 120 is shown in telemetric communication with subcutaneous ICD 110 by a wireless communication link 140. A bidirectional communication link 140 may be established between ICD 110 and programmer 120 using any appropriate RF link such as Bluetooth, WiFi, or Medical Implant Communication Service (MICS). Programmer 120 is used to transmit operating commands, software, or data retrieval requests to IMD 110 and to receive data acquired by IMD 110.

The medical device system 100 includes at least one tissue perfusion monitor 122, 124 or 126 and may additionally or alternatively include a LD unit (not shown in FIG. 4) enclosed within ICD housing 112. Monitors 122 and 124 are illustrated as external monitors worn by the patient as a wearable cuff monitor 122 or a wearable patch monitor 124. Monitor 126 is illustrated as an implantable tissue perfusion monitor that may be implanted at any desired body location for monitoring tissue perfusion. While FIG. 4 shows three tissue perfusion monitors 122, 124 and 126 to illustrate various monitor configurations and locations, it is recognized that only one monitor may be used with ICD 110 or multiple monitors may be used with ICD 110 for cooperatively detecting an unstable or deteriorating hemodynamic condition of patient 102.

Each of the monitors 122, 124 and 126 is shown having a bidirectional communication link 132, 134, and 136, respectively, with ICD 110, which may use any appropriate RF link such as Bluetooth, WiFi, MICS or other wireless communication technology for IMD systems. ICD 110 may request a tissue perfusion measurement from a monitor 122, 124, or 126. Tissue perfusion monitor 122, 124 or 126 responds by performing a measurement and transmitting a measurement signal back to ICD 110.

Subcutaneous ICD 110 is one illustrative embodiment of an implantable medical device that may operate cooperatively with a LDF tissue perfusion monitor for monitoring a patient condition and/or controlling a therapy. The tissue perfusion monitor described herein may be implemented in conjunction with other types of implantable devices configured to detect a physiological condition and/or for automatic therapy delivery, including ICDs coupled to transvenous leads, pacemakers, drug delivery pumps, hemodynamic monitors, ECG monitors, or the like. As such, in other embodiments ICD 110 may be replaced in system 100 by another type of implantable medical device (IMD) incorporating a LD sensing module or in communication with a wireless LD perfusion monitor 122, 124 or 126.

In one embodiment, ICD 110 and lead 114 may be replaced by a dual chamber, biventricular or multi-chamber pacing device and associated transvenous leads. For example, IMD system 100 may alternatively include one or more of tissue perfusion monitors 122, 124, 126 positioned at desired monitoring site(s) and a cardiac pacemaker and associated leads for delivering CRT. A pacemaker and associated leads for delivering CRT is generally disclosed in U.S. Pat. No. 7,092,759 (Nehls, et al.), hereby incorporated herein by reference in its entirety. A LD sensor module 10 or 80 (FIGS. 1 and 3) may be incorporated within the pacemaker, in addition to or alternatively to the wireless monitors 122, 124 and 126.

Figure 5:
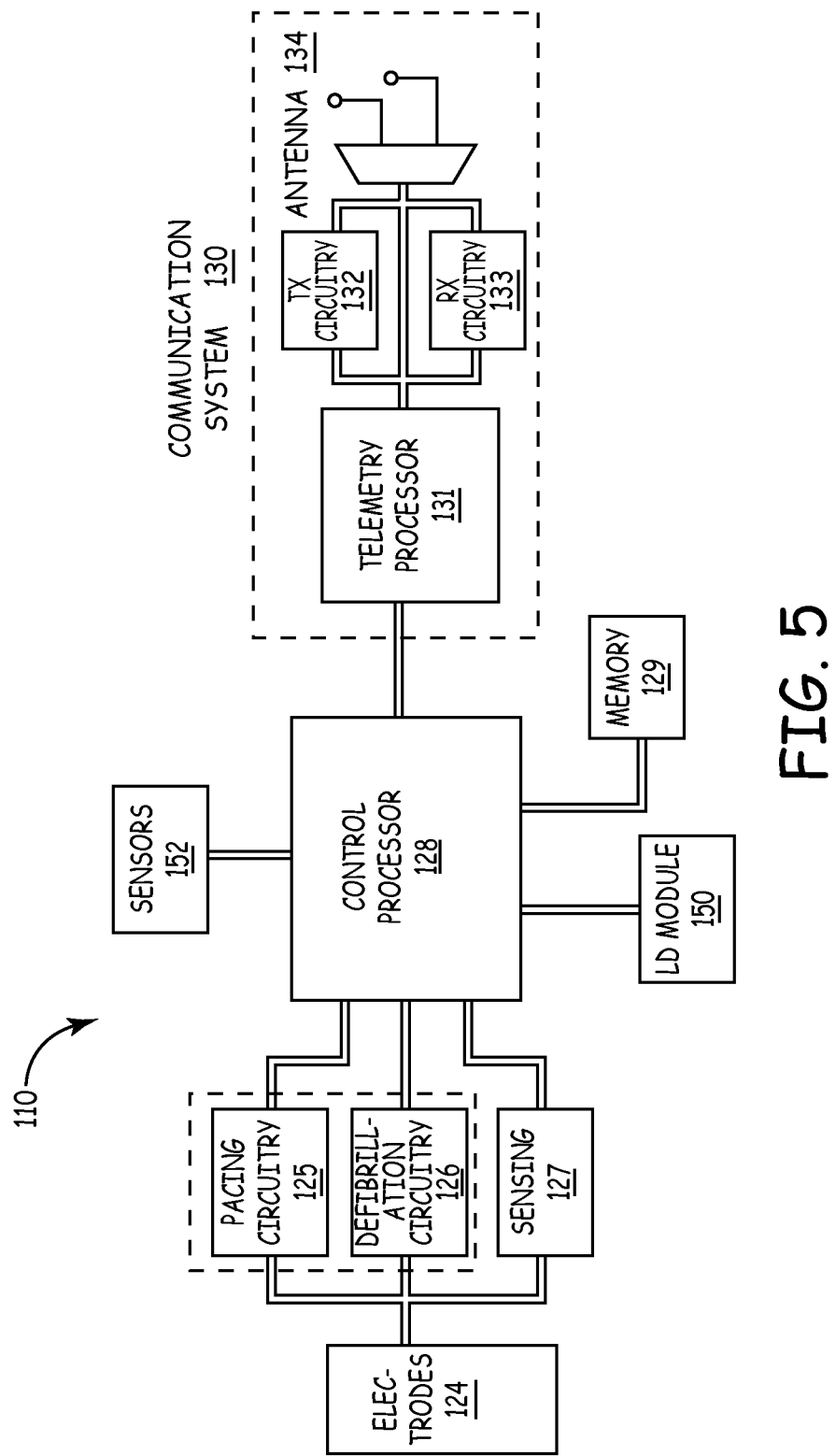
FIG. 5 is a functional block diagram of an ICD.

FIG. 5 is a functional block diagram of ICD 110. Circuitry located within ICD 110 of FIG. 4 includes defibrillation circuitry 126, sensing circuitry 127, and may include pacing circuitry 125. In alternative embodiments, an IMD used in conjunction with a tissue perfusion monitor may include pacing circuitry 125 without defibrillation capabilities. Electrodes 124 carried by leads coupled to ICD 110 and/or incorporated along the ICD housing are connected to pacing circuitry 125, defibrillation circuitry 126 and sensing circuitry 127. Each lead (and in turn individual electrodes associated with each lead) coupled to the ICD may be used in multiple capacities to sense cardiac depolarizations (e.g. P-waves and R-waves), deliver pacing pulses including anti-tachycardia pacing (ATP) pulses, and deliver defibrillation or cardioversion shocks.

Control processor 128 receives input through sensing circuitry 127 from electrodes 124 concerning cardiac depolarizations sensed by the electrodes connected to sensing circuitry 127. Based on input received from sensing circuitry 127, control processor 128 performs an arrhythmia detection algorithm for detecting arrhythmias and selecting a therapy as needed. Therapy may include providing ATP therapy using pacing circuitry 125 and selected pacing electrodes, providing defibrillation or cardioversion shocks using defibrillation circuitry 126 and a selected high voltage electrode, or providing no treatment at all.

Control processor 128 stores selected data to memory 129, and retrieves stored data from memory 129 as necessary. Communication system 130 includes telemetry processor 131, transmission circuitry 132, receiving circuitry 133, and antenna 134. Communication system 130 allows communication between ICD 110 and devices external to the patient as well as a tissue perfusion monitor as described above. In some embodiments, ICD 110 is configured to perform bi-directional telemetric communication with a tissue perfusion monitor for requesting and receiving a tissue perfusion signal. Control processor 128 uses the tissue perfusion signal in detecting an arrhythmia or verifying an arrhythmia detection made based on a cardiac electrical signal. Control processor selects a therapy based at least in part on the tissue perfusion signal. Circuitry included in ICD 110 for controlling the delivery of arrhythmia therapies may correspond to ICD circuitry generally described in commonly-assigned U.S. Pat. No. 6,259,947 (Olson et al.), hereby incorporated herein by reference in its entirety.

In some embodiments, ICD 110 includes a LD sensor module 150 within or along the exterior surface of the housing 112 of ICD 110. When configured inside housing 112, module 150 receives and emits light through a window formed in the ICD housing 112 (FIG. 4). LD sensor module 150 may generally correspond to the sensor module 10 or 80 as described above, though it is recognized that LD sensor module 150, when located within or along an IMD such as ICD 110, may share components such as a power source and processor with other ICD components. LD sensor module 150 is enabled to provide a tissue perfusion signal to control processor 128, which may be delivered through direct wiring without requiring wireless telemetry between LD module 150 and processor 128.

ICD 110 may include or be coupled to other physiological sensors 152, such as an activity sensor, posture sensor, pressure sensor, or the like. Control processor 128 may receive other physiological sensor signals for detecting patient conditions and for use in controlling therapy delivery. In one embodiment, a physiological signal is used by control processor 128 in controlling, at least in part, signal processing methods used by LD sensor module 150. As will be further described below, LD sensor module 150 includes a signal processor that applies one or more narrow bandpass filters to the photodetector current signal for obtaining tissue perfusion measurements. The passband filter(s) used for filtering the photodetector signal may be selected, at least in part, based on another physiological signal obtained from sensors 152, e.g. an activity or posture sensor.

Figure 6:
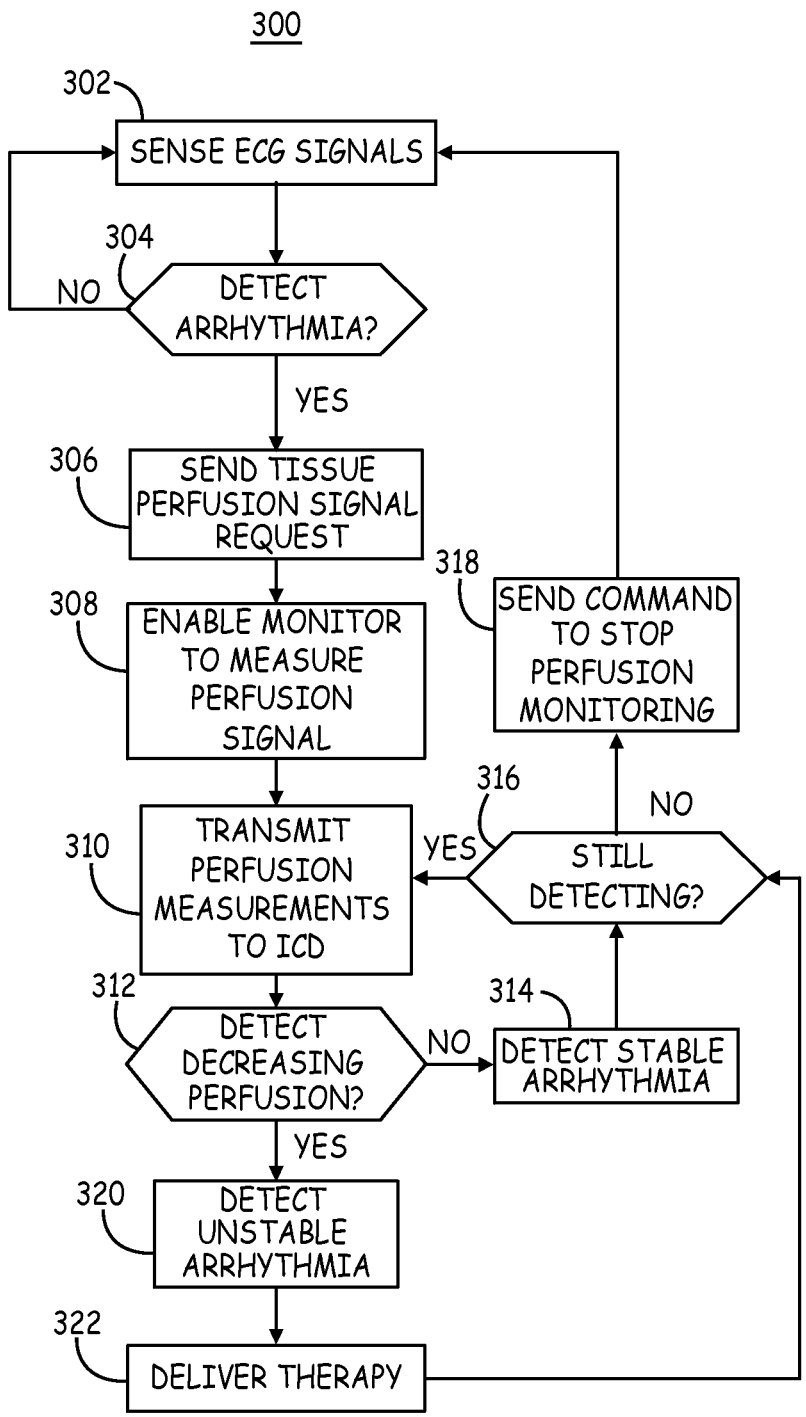
FIG. 6 is a flow chart of a method for monitoring tissue perfusion for use in detecting hemodynamically unstable arrhythmias.

FIG. 6 is a flow chart 300 of a method for monitoring tissue perfusion for use in detecting hemodynamically unstable arrhythmias. Flow chart 300 and other flow charts presented herein are intended to illustrate the functional operation of the device, and should not be construed as reflective of a specific form of software or hardware necessary to practice the methods described. It is believed that the particular form of software, firmware or hardware will be determined primarily by the particular system architecture employed in the device. Providing software, firmware and/or hardware to accomplish the described functionality in the context of any modern implantable medical device system, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The method shown by flow chart 300 is performed by a medical device system including an ICD incorporating an LD sensor module, which may be an implanted or externally worn tissue perfusion monitor, such as the system shown in FIG. 4, or a sensor module incorporated within the ICD itself. At block 302, the ICD senses ECG signals (or EGM signals if intracardiac electrodes are coupled to the ICD) for use in detecting an arrhythmia at block 304 according to detection algorithms implemented in the ICD. An arrhythmia detection algorithm is typically implemented for detecting ventricular tachycardia (VT) or ventricular fibrillation (VF) but other arrhythmias such as supraventricular tachycardia (SVT) may also be detected or discriminated.

When a VT or VF is detected that is potentially hemodynamically unstable and thus requiring a cardioversion/defibrillation shock, the ICD transmits a request for a tissue perfusion signal to the tissue perfusion monitor (or LD sensor module) at block 306. At block 308, the tissue perfusion monitor enables the laser light source to emit light and the monitor processor receives the photodetector signal for determining tissue perfusion measurements. A tissue perfusion measurement may be sampled or measured at regular intervals of time, e.g. once per second, every two seconds, every five seconds or other interval to determine if the detected arrhythmia is associated with a decreasing trend in tissue perfusion.

At block 310, the tissue perfusion measurements are transmitted to the ICD control processor (via wireless telemetry if necessary). The ICD compares the tissue perfusion measurements obtained over a measurement interval to detect a decreasing trend in perfusion at block 312. Tissue perfusion measurements may be sampled several times a second, once per second or less, but will typically be monitored over a short interval of time, for example 30 seconds or less, to enable quick detection of an unstable rhythm requiring shock delivery. If decreasing perfusion is not detected, the arrhythmia is determined to be a hemodynamically stable arrhythmia at block 314. The ICD will withhold ventricular cardioversion/defibrillation therapy. In some embodiments, other therapies, such as anti-tachycardia pacing may be delivered.

If the ICD is still detecting an arrhythmia based on cardiac electrical activity, as determined at decision block 316, the tissue perfusion monitor continues to measure a perfusion signal and transmit the signal to the ICD control processor. A sustained arrhythmia may deteriorate from a hemodynamically stable rhythm to a hemodynamically unstable rhythm. If the ICD is no longer detecting an arrhythmia (decision block 316), the ICD sends a command to the tissue perfusion monitor (i.e., LD sensor module) at block 318 to stop measuring tissue perfusion and stop transmission of the tissue perfusion signal. The process returns to block 302 where the ICD continues to sense the ECG (or EGM) signal for detecting arrhythmias.

If decreasing tissue perfusion is detected at block 312 by the ICD in response to the tissue perfusion signal received from the tissue perfusion monitor, the arrhythmia is detected as an unstable arrhythmia at block 320. The ICD delivers a cardioversion/defibrillation therapy at block 322 to promptly terminate the unstable arrhythmia according to programmed therapy delivery parameters. After delivering the therapy at block 322, if the ICD is still detecting an arrhythmia at decision block 316, the tissue perfusion signal continues to be measured and transmitted to the ICD at block 310. It is understood that multiple shocks may be delivered in some cases in order to terminate the arrhythmia.

If the arrhythmia is no longer detected at block 316, the tissue perfusion monitoring and transmission of the tissue perfusion signal is stopped at block 318 by a command sent from the ICD to the tissue perfusion monitor. The process returns to block 302.

Figure 7:
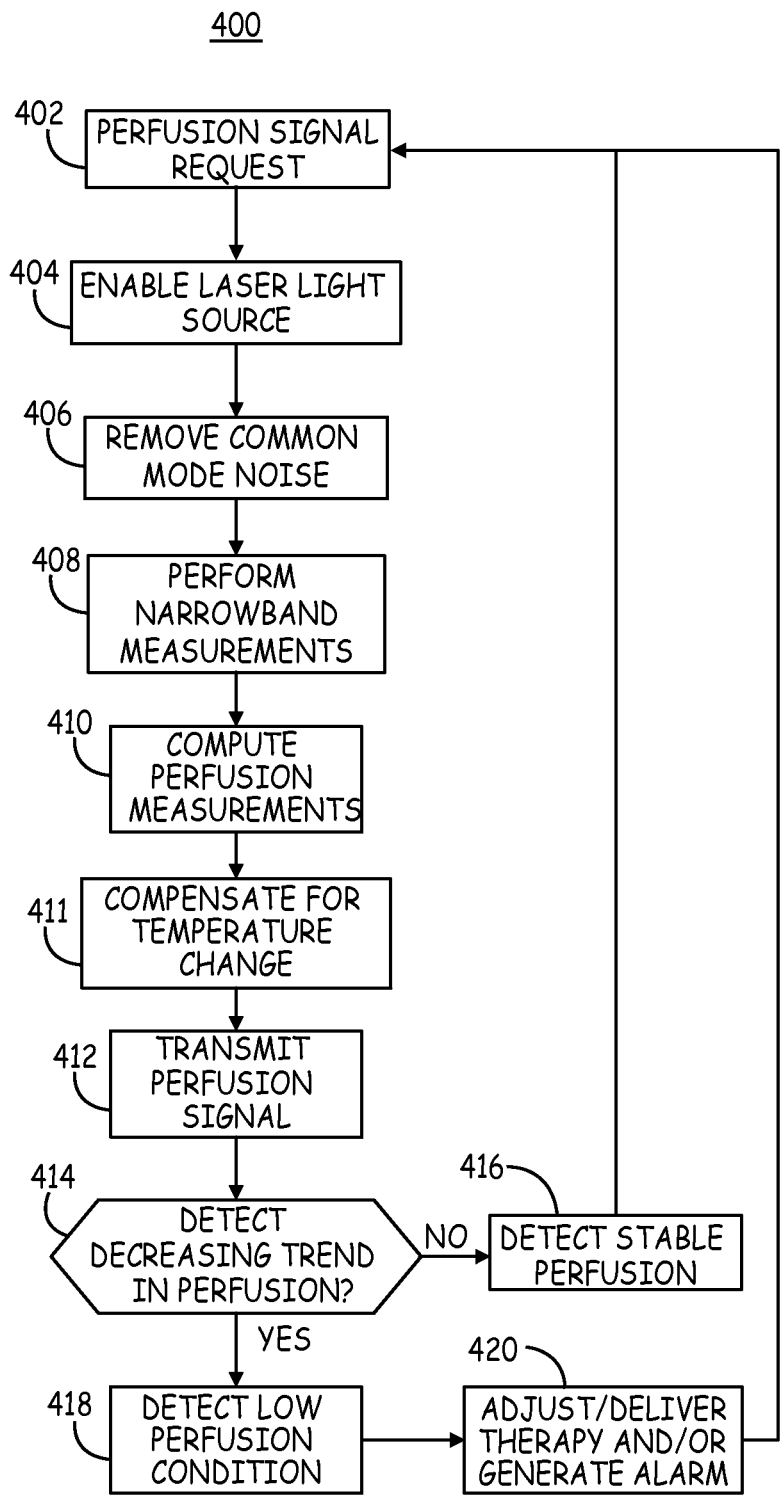
FIG. 7 is a flow chart of one method for measuring a tissue perfusion signal.

FIG. 7 is a flow chart 400 of one method for measuring a tissue perfusion signal. At block 402, the tissue perfusion monitor receives a wireless signal from another medical device indicating a request for a tissue perfusion signal. Alternatively, when a LD sensor module is incorporated within a requesting device, a request signal is sent from the device control processor to the LD sensor. The monitor enables the laser light source to emit light at block 404. At block 406, an induced photodetector current signal undergoes filtering, amplification, and a second photodetector signal may be used to remove common mode noise from the photodetector signal as described previously.

At block 408, the photodetector signal is processed to provide a tissue perfusion measurement at block 410. At block 408, the photodetector signal may be sampled in some embodiments at a relatively high rate, for example a sampling rate between approximately 1 kHz and 15 kHz may be used. In other embodiments, sampling may be less than 1 kHz or more than 15 kHz as required for a particular monitoring application. The sampling rate selected will depend at least in part on the processing power and available power supply of the LD sensor module. In still other embodiments, the photodetector signal is used as an analog signal in the initial signal processing steps.

LD signal processing performed at block 408 includes narrowband filtering of the photodetector signal by one or more narrowband bandpass filters. The bandpass signal(s) are then used to obtain a tissue perfusion measurement at a desired sampling rate, which may be several times per second, once per second or less often as required by a monitoring algorithm. For example, perfusion measurements may be sampled from passband signal(s) every second for a desired interval of time allowing the perfusion measurements to be compared to each other for detecting an increasing, decreasing or stable trend in tissue perfusion. In one example, the tissue perfusion measurement is the sampled magnitude (or power) of the passband signal(s).

Alternatively, the passband signal(s) may be sampled over a defined interval of time and sample points averaged together to obtain an average perfusion measurement for a measurement interval. An averaged measurement can be compared to an average perfusion measurement obtained for an earlier time period. Average tissue perfusion measurements may be obtained according to a periodic tissue perfusion monitoring algorithm or in response to a trigger based on another physiological signal or a change in a delivered therapy. For example, perfusion measurements may be determined once per second for five to ten seconds or more then averaged to obtain an average tissue perfusion measurement for a given time interval. Averaged perfusion measurements obtained once per hour, every four hours, every eight hours, once per day, once per week, or other scheduled time interval may be compared to determine trends in tissue perfusion over relatively longer periods of time. It is recognized that the time intervals for determining a tissue perfusion measurement and time intervals between measurements being compared will vary depending upon the particular monitoring application. Other examples of methods for obtaining perfusion measurements at block 410 from one or more passband signals are described below.

The tissue perfusion signal may be compensated or corrected for temperature changes at block 411. A signal received from a temperature sensor and correlated to changes in temperature at the monitoring site is used by the monitor processor to adjust the tissue perfusion measurements according to temperature changes. A temperature correction factor may be determined prospectively during a sensor calibration procedure in which the temperature sensor response and the tissue perfusion sensor response to known changes in actual temperature are recorded. Alternatively, temperature data is stored along with tissue perfusion measurements to allow changes in perfusion to be interpreted in light of temperature changes.

The temperature-compensated tissue perfusion signal is transmitted from the tissue perfusion monitor to the requesting device at block 412 (or from the LD sensor module to a control processor when implemented in a single IMD). The requesting device compares perfusion measurements sampled over time at block 414. If the tissue perfusion signal is decreasing, decreasing or low perfusion is detected at block 418. If not, stable perfusion is detected at block 416. Alternatively the perfusion measurement comparison may be performed by a comparator included in a tissue perfusion monitor and a signal indicating decreasing perfusion, increasing perfusion, or stable perfusion is transmitted to the requesting device.

In response to detecting a low perfusion condition, i.e. a decreasing perfusion trend, a therapy is adjusted or delivered at block 420. In the case of the requesting device being an ICD, a cardioversion/defibrillation shock may be delivered at block 420 based on the verification of a hemodynamically unstable arrhythmia as evidenced by a decreasing tissue perfusion signal. In other embodiments, a comparative analysis of tissue perfusion measurement obtained during a cardiac pacing optimization procedure may be performed to identify pacing or CRT parameters that yield the highest or optimal tissue perfusion. The pacing or CRT pacing parameters are adjusted to the optimal settings at block 420.

The perfusion measurement may be used as a surrogate for cardiac output or blood pressure measurements in any therapy management application. A therapy may be optimized or adjusted to maintain an optimal hemodynamic status of the patient. A method for optimizing CRT which may be adapted to implement a tissue perfusion measurement as described herein is generally described in U.S. Pat. No. 7,769,451 (Yang, et al.), hereby incorporated herein by reference in its entirety.

In addition or alternatively to adjusting or delivering a therapy at block 420, the control processor of the requesting device may make a decision to generate a patient or clinician alarm at block 420 to notify the patient or clinician of the low perfusion condition. In particular, when a LD sensor module is incorporated in a medical device system for monitoring a medical condition without therapy delivery conditions, a patient may be warned of a low perfusion condition that may warrant medical attention.

As such, the tissue perfusion monitor described herein may be implemented in systems used for treating patients for cardiac arrhythmias, heart failure, or hypertension among other conditions. A tissue perfusion monitor may be used for monitoring perfusion in other conditions such as diabetes, peripheral vascular disease, stroke, etc., that are known to cause changes in local or systemic perfusion of body tissues. Furthermore, a tissue perfusion monitor or IMD incorporating an LD sensor as described herein may be implemented in systems that do not include therapy delivery capabilities. The tissue perfusion measurements may be monitored and recorded over time for detecting heart failure decompensation or other hemodynamic events that manifest in decreased tissue perfusion.

Figure 8:
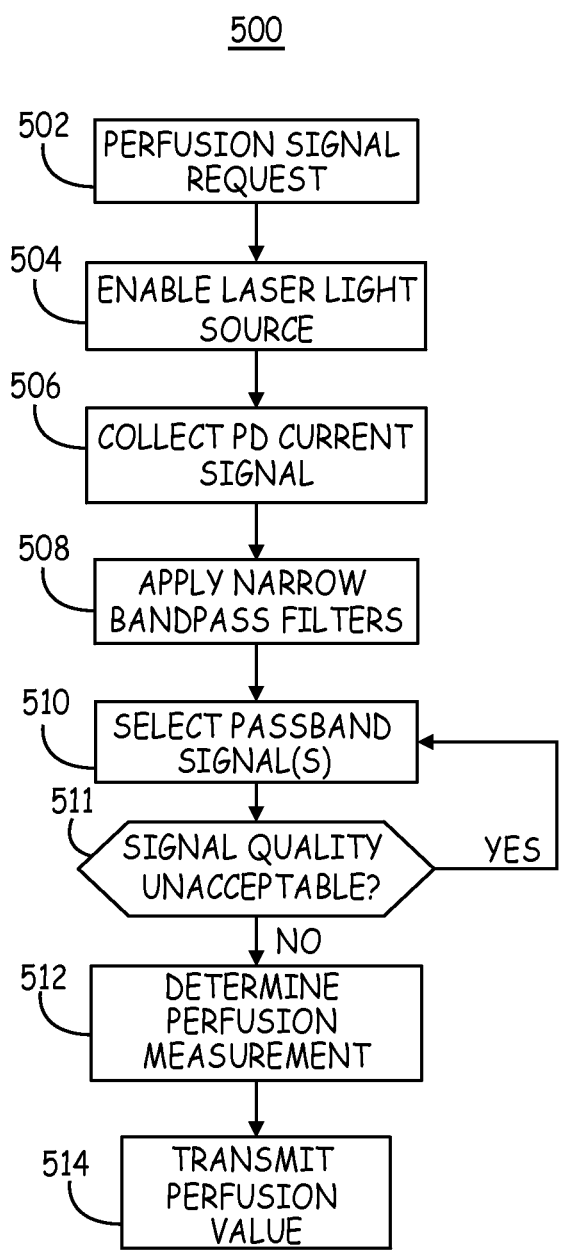
FIG. 8 is a flow chart of a method for performing tissue perfusion measurements using a laser Doppler flow sensor signal.

FIG. 8 is a flow chart 500 of a method for performing tissue perfusion measurements using a LD flow sensor signal according to one embodiment. At block 502, a perfusion signal request is transmitted by a requesting device, which may be an IMD or an external device. The perfusion signal request may indicate when (immediately or at some future time) and for how long a signal is requested (e.g. several seconds, minutes, or continuously until further notice. Alternatively, upon receiving a perfusion signal request the LD sensor module transmits a tissue perfusion signal for a default period of time or transmits a derived perfusion measurement.

In response to receiving the perfusion signal request, the LD sensor module enables its light source at block 504 to begin emitting light and collects the resulting photodetector current signal at block 506. The photodetector current signal is typically sampled at a relatively high sampling rate, for example approximately 1 kHz or more. Instead of performing a full spectral analysis on the photodetector signal, which is typically done in LDF and imposes significant processing and power burden, one or more narrow bandpass filters are applied to the sampled photodetector current signal at block 508.

In one embodiment, a narrow bandpass filter is provided with a bandwidth of approximately 400 Hz or less, e.g., a narrower bandwidth may be used of approximately 50 Hz, 100 Hz, or 200 Hz. The applied filter is a Butterworth bandpass filter in one example though other filters may be used.

When multiple bandpass filters are used, each filter is centered on a different frequency. In one embodiment, four bandpass filters are used with each filter centered at spaced apart center frequencies, for example ranging from approximately 100 Hz to over 1000 Hz. Different passbands centered on different frequencies will contain different blood flow information corresponding to different ranges of blood flow velocity in the measurement volume. For example, a passband centered at approximately 250 Hz may provide information relating to blood components flowing at rates on the order of approximately 0.1 mm/sec and a passband centered at approximately 1000 Hz may provide information relating to blood components flowing at a rate of 0.4 mm/sec (when a near infrared light source is used). Different passbands can be used to obtain information relating to the behavior of different blood flow velocity ranges. One or more narrow bandpass filters may be implemented using analog or digital circuitry in the processor of the tissue perfusion monitor and/or the control processor of the associated IMD.

At block 510, one or more passbands are selected for signal analysis. Depending on the condition being monitored, the blood flow velocity information contained in a particular velocity range may be of greater interest than other velocity ranges. For example, if the behavior of higher velocity components presents an earlier or greater response to a monitored condition than other velocity ranges, a narrow bandwidth corresponding to a higher frequency of the photodetector current signal may be selected. If the behavior of lower velocity components is of greater interest, a lower frequency passband may be selected.

Selection of one or more passbands may be performed once, e.g., as part of an initial device set-up, based on the device requesting the perfusion signal and the condition being monitored. If multiple devices included in a patient monitoring or therapy delivery system are making requests for perfusion signals, the passband signal(s) may be selected each time a perfusion signal is requested based on the requesting device. In other embodiments, a single requesting device may be monitoring more than one condition. When a perfusion signal request is made at block 502, the purpose for the request may be indicated or one or more passband(s) may be directly specified by the requesting device to guide selection at block 510.

In still other embodiments, a clinician may test the perfusion signal obtained from different passbands at the time of positioning the LD sensor or during patient follow-up visits and select a passband providing the best signal for monitoring a patient condition. The optimal frequency bandwidth may be patient specific and passband selection may be tailored to an individual patient. The clinician may program the control processor of the LD sensor to store selected passband(s) which are retrieved at block 510. It is understood that in alternative embodiments, passband selection may be performed prior to applying narrow bandpass filter(s) at block 508 such that only the desired passband signals are obtained using selected filters.

A determination as to whether the signal quality of a selected passband is acceptable is performed at block 511. In response to an unacceptable passband signal quality, a different passband is selected at block 510 (or if multiple passbands are selected an unacceptable passband may be ignored). Unacceptable signal quality may be determined based on passband signal magnitude being outside an established physiological range or inferred based on another physiological signal such as an activity signal, posture signal, temperature signal, heart rate, or pressure signal. As such, another physiological signal may be used to indicate which passband(s) are most desirable for use in determining a perfusion measurement.

At block 512, a perfusion measurement is determined and transmitted to the control processor at block 514. In one embodiment, the perfusion measurement is the sampled magnitude, also referred to herein as "power", of a singly selected bandpass filter output signal. For typical physiological monitoring applications, the signal may be sampled and transmitted at a relatively low frequency, for example in the range of 0.5 to 10 Hz. The magnitude of a selected passband signal is transmitted at a 1 Hz sampling rate as a tissue perfusion measurement signal in one illustrative embodiment.

In alternative embodiments, multiple passbands are selected and may be averaged, compared or otherwise combined in any combination to determine a perfusion measurement at block 512. For example, two or more passband signals may be averaged together or combined in a weighted combination to obtain a perfusion measurement signal that is then sampled at a desired sampling rate to obtain tissue perfusion measurements. In another example, multiple passband signals may be averaged individually over a given time interval then the time interval averages may be combined or averaged to obtain a signal tissue perfusion measurement for a give time interval. Alternatively, multiple passband signals may be compared to confirm a trend observed in a primary passband signal that is used to derive the perfusion measurement. A perfusion measurement may be accepted or rejected based on confirmation of a measured trend in one passband using trends measured in another passband(s). It is recognized that numerous variations for obtaining a tissue perfusion measurement from one or more narrow bandpass filter signals obtained from a photodetector signal as disclosed herein may be conceived and such variations are considered within the scope of the present disclosure.

Figure 9:
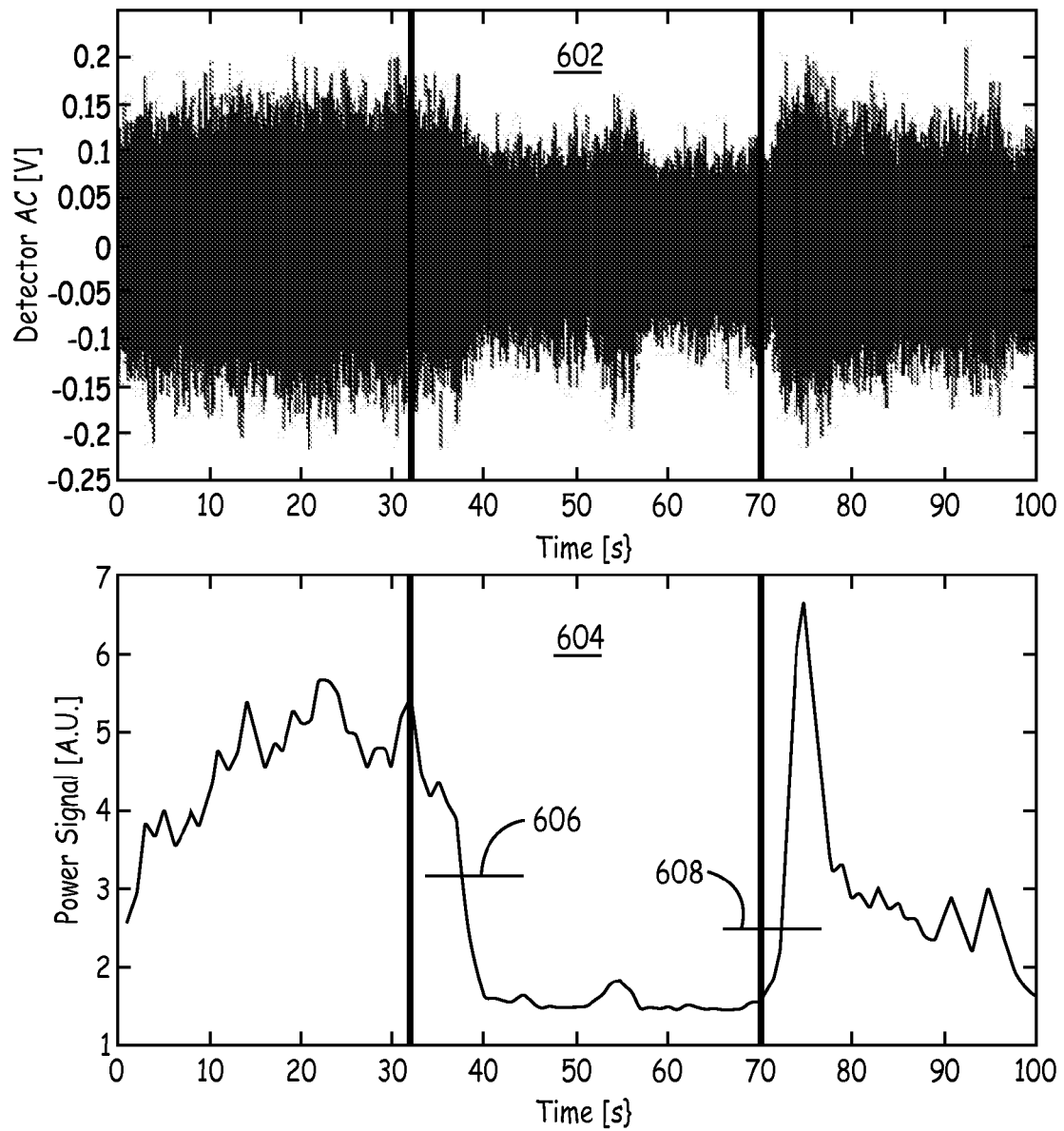
FIG. 9 is a plot of a laser Doppler sensor signal measured along the palm of a hand during an arm cuff test.

FIG. 9 is a plot 602 of a laser Doppler sensor signal measured along the palm of a hand during an arm cuff occlusion test and illustrates the disclosed signal processing methods. The photodetector signal 602 is sampled at 30 kHz. A tissue perfusion measurement signal 604 is obtained by applying a fifth order Butterworth bandpass filter having a narrow passband of 1300 to 1700 Hz to the photodetector signal and sampling the output of the bandpass filter at a sampling rate of 1 Hz. A marked decrease in the perfusion signal 604 is observed to begin at approximately 30 s, corresponding to the time of arm cuff occlusion. At approximately 70 s, the arm cuff pressure is released and a return in perfusion is observed based on the rise of the perfusion measurement signal 604.

The perfusion measurement signal 604 demonstrates that a narrow bandpass filtered signal may be sampled at a relatively low sampling rate, e.g. approximately 1 Hz, to allow a tissue perfusion condition to be detected without the use of high processing burden algorithms that require high frequency sampling rates and spectral analysis of the photodetector output signal. The signal processing steps performed up to the point of power signal sampling of the narrow bandpass signal, i.e., the steps of filtering, amplification, etc., can be implemented using analog circuitry, which may reduce cost and complexity of the sensor module.

A threshold 606 for detecting insufficient or a decrease in perfusion may be established through clinical testing of a population of patients or uniquely established for an individual patient during a clinical office visit or over time. A threshold 608 for detecting a return of tissue perfusion or normal perfusion after a low perfusion condition may likewise be established. The threshold 608 for detecting normal or restored perfusion may be established to be higher, lower or the same as the threshold 606 for detecting insufficient perfusion. Thresholds or criteria set for detecting a physiological condition may be defined as a percentage or relative change from a baseline or initial measurement. Thresholds will typically be defined as a relative change or trend in the tissue perfusion signal.

Figure 10:
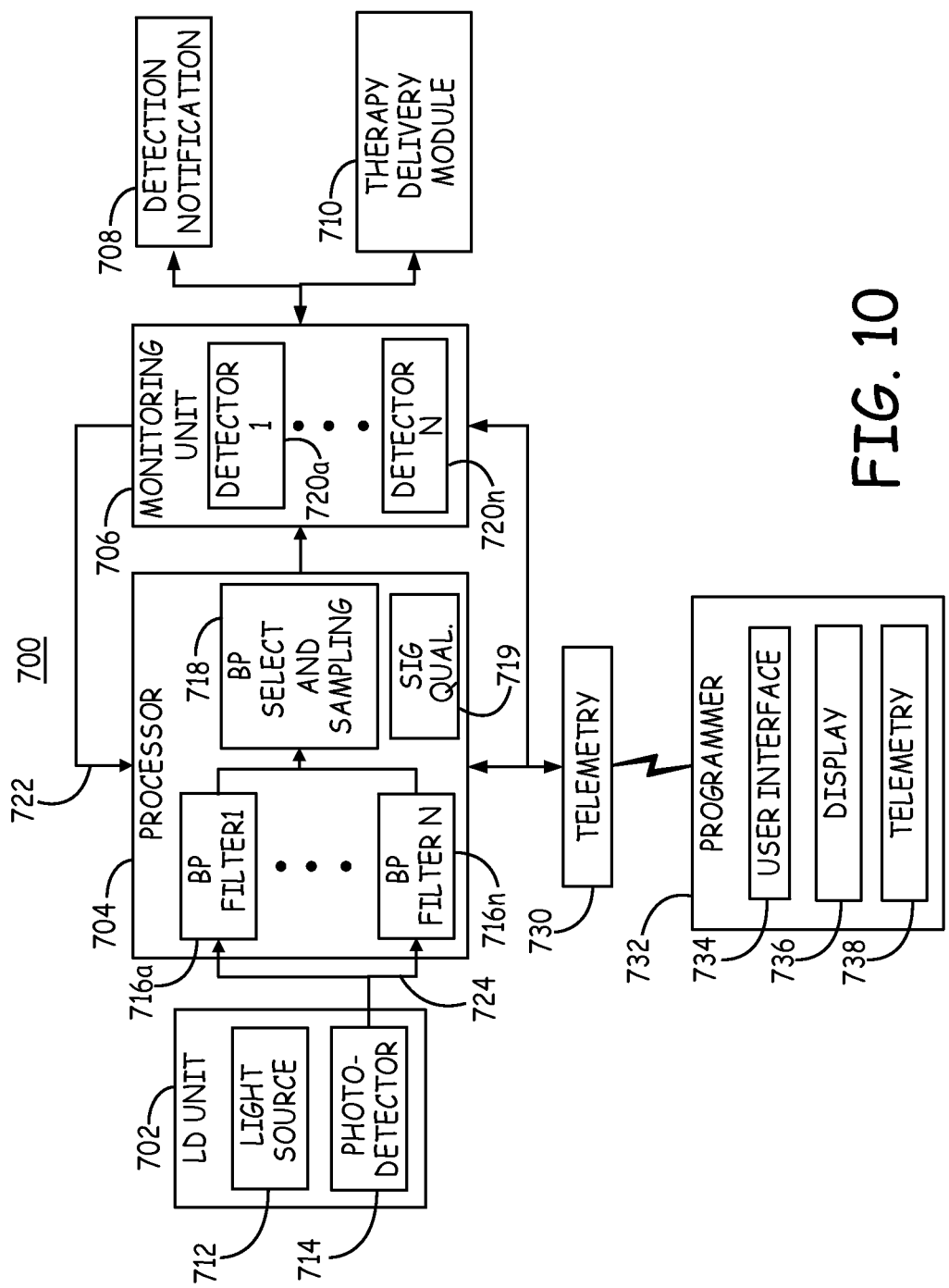
FIG. 10 is a functional block diagram of a medical device system including a laser Doppler (LD) unit according to one embodiment.

FIG. 10 is a functional block diagram 700 of a medical device system including a LD sensor unit 702 according to one embodiment. The system 700 also includes a signal processor and control unit 704, a monitoring unit 706, a detection notification module 708 and/or a therapy delivery module 710.

The LD sensor unit 702 includes a light source 712 and photodetector 714. Dedicated control circuitry may be included in unit 702 for controlling light source 712 and photodetector 714. Alternatively, the processor and control 704 may provide signals to LD unit 702 to control light emission by light source 712.

Signal processor and control 704 receives the photodetector signal 724. Processor and control 704 includes one or more narrow bandpass filters 716a through 716n. As described above the narrow bandpass filters each have a distinct center frequency and may have the same or uniquely defined bandwidths. The bandwidths are relatively narrow, for example up to approximately 1 kHz bandwidth or narrower.

Signal processor and control 704 includes a passband selection and tissue perfusion measurement module 718 for selecting a passband signal from one or more of the outputs of filter 716a through 716n. Alternatively, signal processor and control 704 may select a passband first then apply the one or more selected bandpass filters to the photodetector signal 724.

Processor and control 704 may select the passband in response to a request signal 722 provided by monitoring unit 706 establishing a passband selection, which may include outputs from one or more of filters 716a through 716n. The request signal may be received by processor 704 and/or LD unit 702 to initiate LD signal monitoring, determination of a tissue perfusion measurement, and transmission of the tissue perfusion measurement to the monitoring unit 706. Alternatively, the bandpass selection is established and stored in programmable memory of processor 704. The bandpass selection may be established as a default selection based on the type of monitoring unit 706 included in system 700.

Alternatively, the bandpass selection may be established by a user programming the selection into memory associated with signal processor and control 704 using a programmer 732. Programmer 732 includes a user interface 734, which may be a mouse, touch screen, key pad or the like, a display 736, and telemetry circuitry 738. Telemetry circuitry 738 is configured for bidirectional communication with a telemetry module 730 configured to operate in conjunction with processor 704 and monitoring unit 706 for sending and receiving data relating to a physiological condition monitoring function. A user may perform measurements of the photodetector signal to determine an optimal passband or combination of passband signals for determining a tissue perfusion measurement. As such the passband selection may be tailored to an individual patient based on individualized measurements and monitoring, established based on clinical data obtained from a population of patients, or set according to a monitoring unit function.

A signal quality analysis module 719 may be included in processor 706 for determining if a selected passband signal is acceptable or determining when a different secondary passband should be used in place of a primary passband selection. For example, if a selected passband signal is found to have a signal amplitude outside a normal operating or physiological range, the passband signal is suspected to be contaminated. A different passband may be selected. Alternatively, indicators of signal quality may be used by module 719, such as a patient activity signal. If the patient activity is low, a passband associated with a lower end of the blood flow velocity range may be a preferred passband to use. However if patient activity is high, a different passband associated with a higher portion of the blood flow velocity range may be preferred as the selected passband for determining a tissue perfusion measurement. Selection of a different passband may be performed to avoid or minimize noise or artifact that may have a greater effect on the signal-to-noise ratio in some passbands than others. For example, a different passband may be selected during high activity to avoid or minimize the effects of motion artifacts in the signal which can be present with high activity.

Processor and control 704 determines a tissue perfusion measurement for transmission to monitoring unit 706. In some embodiment, monitoring unit 706 may include one or more implantable or external medical devices, or any combination thereof, configured to monitor and detect a physiological condition of a patient. In various embodiments, LD unit 702, processor and control 704, monitoring unit 706 and detection notification and therapy delivery module 710 may be incorporated in a single implantable or external device or distributed across multiple devices.

BP selection and sampling module 718 may determine a tissue perfusion measurement as the magnitude (or power) of a selected passband signal or any combination (summed, averaged, weighted combination, difference, ratio, etc.) of two or more selected passband signals. A tissue perfusion measurement may thus be transmitted to monitoring unit 706 as a sampled magnitude of a passband signal or combination of passband signals. The tissue perfusion measurement may be transmitted, for example, as an analog or digitally-converted magnitude of the passband signal sampled at a desired sampling rate for the particular monitoring application, for example at approximately 1 Hz. The monitoring unit 706 may provide a termination signal on request signal line 722 for terminating a tissue perfusion measurement signal when enough data has been received for detecting a physiological condition. Alternatively, an initial request sent on signal line 722 may include an interval of time for transmitting a tissue perfusion measurement signal, e.g. for 10 seconds, one minute, or another time period.

In other embodiments, the processor 704 may compute a tissue perfusion measurement that is transmitted to monitoring unit 706. For example, processor 704 may select multiple passband signals, average the signals to obtain a single signal, and then average the single signal over time to obtain a single value representing a tissue perfusion measurement for a measurement time interval. In an illustrative example, four bandpass filters may be applied to the photodetector signal. At each sample time point, four different points, one from each bandpass filter, are available in the power spectra of the photodetector signal. These four points may be averaged or combined to determine a perfusion measurement at a given sample time point.

Alternatively, each passband signal may be averaged over a period of time, to obtain a time averaged measurement for a given passband signal then the time-averaged signal values may be combined in an average, weighted or other mathematical combination for determining a signal tissue perfusion measurement that is transmitted to monitoring unit 706.

The monitoring unit 706 may include multiple detector modules 720a through 720n which are configured to monitor and detect different physiological conditions. For example, one detector 720a may be configured to detect unstable ventricular tachycardia or fibrillation, another detector 720n may be configured to detect a hemodynamic condition relating to heart failure. Any of detectors 720a through 720n may transmit a request signal to processor 704, which may establish the passband signal(s) to be used for determining perfusion measurement.

If detector 720a is detecting hemodynamically unstable cardiac arrhythmias, detector 720a may send a request signal to processor 704 due to a preliminary detection based on ECG or EGM signals. The request signal may establish a passband corresponding to a relatively low frequency associated with low blood flow velocity, which may provide the earliest response time to an unstable arrhythmia condition. If detector 720n is detecting a heart failure condition, a passband signal corresponding to a higher center frequency may be selected because the response of higher blood flow velocity components may be more responsive to changes associated with the heart failure condition or to a heart failure therapy. In other words, the passband signal(s) selected may be established according to associated blood flow velocity components that are found to provide the greatest sensitivity or earliest response to a particular physiological condition being monitored. The passband signal selections may be established according to clinical evaluation of an individual patient or previously established based on clinical studies of a population of patients.

Detectors 720a through 720n may be implemented in a single device or separate devices. Monitoring unit 706 determines whether to issue a detection notification or warning 708 and/or adjust a therapy delivered by therapy delivery module 710 in response to the tissue perfusion signal. It is understood that monitoring unit 706 may receive other signal inputs, such as ECG or EGM signals, pressure signals, oxygen signals, acoustical signals or other physiological signals sensed by sensors (not shown in FIG. 10 but as earlier described in conjunction with FIG. 5) coupled to monitoring unit 706.

Detection notification 708 may issue a patient alarm or store data associated with a detected event for immediate or future transmission to programmer 732. Therapy delivery module 710 may deliver an electrical stimulation therapy, a drug therapy, a biological fluid, or a combination thereof.

Thus, a medical device system incorporating LDF and associated methods have been presented in the foregoing description with reference to specific embodiments. It is appreciated that various modifications to the referenced embodiments may be made without departing from the scope of the disclosure as set forth in the following claims.

The invention claimed is:

1. A medical device system for monitoring tissue perfusion in a patient, comprising:
   a laser Doppler unit comprising a coherent laser light source and a photodetector;
   a signal processor comprising a plurality of bandpass filters each having a distinct center frequency and bandwidth, wherein the signal processor is configured to receive a signal from the photodetector, apply the bandpass filters to the photodetector signal, and select a first passband signal output from a first one of the plurality of filters to determine a tissue perfusion measurement from the filtered signal;
   and a monitoring unit configured to receive the tissue perfusion measurement and to detect a physiological condition of the patient in response to the tissue perfusion measurement.

2. The system of claim 1, wherein the monitoring unit is further configured to transmit a request signal, and wherein the laser Doppler unit and the signal processor are configured to cooperatively perform tissue perfusion monitoring and determine the tissue perfusion measurement responsive to the request signal and transmit the tissue perfusion measurement to the monitoring unit.

3. The system of claim 2, wherein the tissue perfusion measurement comprises a sampled magnitude of to the first passband signal output.

4. The system of claim 1, wherein the monitoring unit is further configured to transmit a request signal, wherein the request signal establishes a passband selection and the signal processor selects the first passband signal in response to the request signal.

5. The system of claim 4, wherein the monitoring unit comprises a first unit for detecting a first condition and a second unit for detecting a second condition different than the first condition, and wherein the first monitoring unit is configured to transmit a request signal establishing a first passband selection corresponding to a tissue perfusion measurement for detecting the first condition, and the second monitoring unit is configured to transmit a request signal establishing a second passband selection different than the first passband selection and corresponding to a tissue perfusion measurement for detecting the second condition.

6. The system of claim 1, wherein the signal processor is further configured to select a second passband signal and determine the tissue perfusion measurement using both the first and the second passband signal.

7. The system of claim 1, wherein the processor is further configured to select a passband selection established by a user, and further comprising a programmable memory for storing the selected established passband.

8. The system of claim 1, wherein the processor is further configured to determine unacceptable signal quality of the first passband signal and select a second passband signal for determining the tissue perfusion measurement in response to determining the unacceptable signal quality.

9. The system of claim 1, wherein the monitoring unit is configured to detect a first state of the physiological condition using a first threshold established for the perfusion measurement and detect a second state of the physiological condition using a second threshold established for the perfusion measurement, the second threshold different than the first threshold.

10. A method for monitoring a patient using a medical device system comprising a laser Doppler unit, the method comprising:
   controlling the laser Doppler unit to emit light from a coherent laser light source;
   collecting a photodetector signal produced by the laser Doppler unit using a signal processor comprising a plurality of bandpass filters each having a distinct center frequency and bandwidth;
   applying the bandpass filters to the photodetector signal and selecting a first passband signal output from a first one of the plurality of filters to determine a tissue perfusion measurement from the filtered signal;
   and enabling a monitoring unit to receive the tissue perfusion measurement and detect a physiological condition of the patient in response to the tissue perfusion measurement.

11. The method of claim 10, further comprising:
transmitting a request signal; and
responsive to the transmitted request signal, controlling the laser Doppler unit and the signal processor to cooperatively perform tissue perfusion monitoring and determine the tissue perfusion measurement and transmit the tissue perfusion measurement to the monitoring unit.

12. The method of claim 11, wherein determining the tissue perfusion measurement comprises sampling a magnitude of the first passband signal output.

13. The method of claim 10, further comprising:
transmitting a request signal, wherein the request signal establishes a passband selection; and
selecting the first passband signal in response to the request signal.

14. The method of claim 13, further comprising:
detecting a first condition and a second condition different than the first condition;
transmitting a request signal establishing a first passband selection corresponding to a tissue perfusion measurement for detecting the first condition; and
transmitting a request signal establishing a second passband selection different than the first passband selection and corresponding to a tissue perfusion measurement for detecting the second condition.

15. The method of claim 10, further comprising:
selecting a second passband signal; and
determining the tissue perfusion measurement using both the first and the second passband signal.

16. The method of claim 10, further comprising:
storing a passband selection established by a user; and
selecting the established passband.

17. The method of claim 10, further comprising:
determining an unacceptable signal quality of the first passband signal;
selecting a second passband signal in response to determining the unacceptable signal quality; and
determining the tissue perfusion measurement in response to the second passband signal.

18. The method of claim 10, further comprising:
detecting a first state of the physiological condition using a first threshold established for the perfusion measurement; and
detecting a second state of the physiological condition using a second threshold established for the perfusion measurement, the second threshold different than the first threshold.

19. A non-transitory computer-readable medium storing a set of instructions which cause a medical device system comprising a laser Doppler unit to perform a method comprising:
controlling the laser Doppler unit to emit light from a coherent laser light source;
collecting a photodetector signal produced by the laser Doppler unit using a signal processor comprising a plurality of bandpass filters each having a distinct center frequency and bandwidth;
applying the bandpass filters to the photodetector signal;
selecting a first passband signal output from a first one of the plurality of filters to determine a tissue perfusion measurement from the filtered signal;
and enabling a monitoring unit to receive the tissue perfusion measurement and detect a physiological condition of the patient in response to the tissue perfusion measurement.

* * * * *